(12) United States Patent
Barousse et al.

(10) Patent No.: US 12,215,305 B2
(45) Date of Patent: Feb. 4, 2025

(54) TISSUE-PROCESSING CONTAINER FOR AUTOMATED PROCESSING OF TISSUE, METHODS OF USE THEREOF, AND SYSTEMS COMPRISING THE SAME

(71) Applicant: Axogen Corporation, Alachua, FL (US)

(72) Inventors: Daniel Barousse, Gainesville, FL (US); Gerhard Andrew Foelsche, Rehoboth, MA (US)

(73) Assignee: Axogen Corporation, Alachua, FL (US)

( * ) Notice: Subject to any disclaimer, the term of this patent is extended or adjusted under 35 U.S.C. 154(b) by 0 days.

(21) Appl. No.: 18/441,108

(22) Filed: Feb. 14, 2024

(65) Prior Publication Data
US 2024/0182829 A1  Jun. 6, 2024

Related U.S. Application Data

(62) Division of application No. 17/023,229, filed on Sep. 16, 2020, now Pat. No. 11,932,837.

(Continued)

(51) Int. Cl.
*C12M 1/00* (2006.01)
*B65D 21/00* (2006.01)
(Continued)

(52) U.S. Cl.
CPC ............ *C12M 21/08* (2013.01); *C12M 23/44* (2013.01); *C12M 25/10* (2013.01); *C12M 29/10* (2013.01);
(Continued)

(58) Field of Classification Search
CPC ...... C12M 21/08; C12M 23/44; C12M 25/10; C12M 29/10; C12M 45/02; C12M 45/09;
(Continued)

(56) References Cited

U.S. PATENT DOCUMENTS

| 5,154,303 A | 10/1992 | Jordan |
| 2018/0064852 A1 | 3/2018 | Assell et al. |
| 2018/0368623 A1 | 12/2018 | Cerasani |

FOREIGN PATENT DOCUMENTS

| CN | 109415677 A | 3/2019 |
| JP | 2000107035 A | 4/2000 |

(Continued)

OTHER PUBLICATIONS

International Search Report and Written Opinion issued in International Application No. PCT/US2020/051174, issued Feb. 4, 2021 (15 pages).

*Primary Examiner* — Liban M Hassan
(74) *Attorney, Agent, or Firm* — Bookoff McAndrews, PLLC

(57) ABSTRACT

Tissue-processing containers are disclosed for facilitating multistep processing of tissue. Also disclosed are systems incorporating the tissue-processing containers that include shakers, incubators, controllers, and pumps. Multistep methods are disclosed for processing tissues using the tissue-processing containers. The tissue-processing containers are specially designed to achieve efficiencies in automated tissue processing, exposure of tissues to processing media, and multistep tissue processing protocols. The described tissue-processing containers comprise a cup-like cavity comprising a middle hole covered by a mesh screen, troughs for separate processing steps, and are stackable in a substantially airtight and substantially watertight manner. Tissues for processing using the described tissue-processing containers include nerve tissue. Also described herein is a transport housing for the transport of stacks of tissue-processing containers, and which may directly incubate those containers, or which may be placed inside a separate incubator for incubating the containers.

18 Claims, 6 Drawing Sheets

Related U.S. Application Data

(60) Provisional application No. 62/901,733, filed on Sep. 17, 2019.

(51) Int. Cl.
*C12M 1/12* (2006.01)
*C12M 1/33* (2006.01)
*C12M 3/00* (2006.01)

(52) U.S. Cl.
CPC ............ *C12M 45/02* (2013.01); *C12M 45/09* (2013.01); *C12M 47/04* (2013.01); *B65D 21/00* (2013.01)

(58) Field of Classification Search
CPC ...... C12M 47/04; C12M 25/14; C12M 27/10; C12M 45/05; B65D 21/00; A61B 2050/3007; A61B 50/30
See application file for complete search history.

(56) References Cited

FOREIGN PATENT DOCUMENTS

| | | | | |
|---|---|---|---|---|
| JP | 2005506526 | A | 3/2005 | |
| JP | 2016013079 | A | 1/2016 | |
| JP | 2017104077 | A | 6/2017 | |
| JP | 2017105522 | A | 6/2017 | |
| WO | 9207061 | A1 | 4/1992 | |
| WO | WO-2017221665 | A1 * | 12/2017 | ............. B65D 77/06 |

\* cited by examiner

TISSUE-PROCESSING CONTAINER FOR AUTOMATED PROCESSING OF TISSUE, METHODS OF USE THEREOF, AND SYSTEMS COMPRISING THE SAME

CROSS-REFERENCE TO RELATED APPLICATIONS

This application is a divisional of U.S. Non-Provisional Application Ser. No. 17/023,229, filed on Sep. 16, 2020, which claims priority to U.S. Provisional Application No. 62/901,733, filed on Sep. 17, 2019, the entireties of which are incorporated by reference.

GOVERNMENT LICENSE RIGHTS TO CONTRACTOR-OWNED INVENTIONS MADE UNDER FEDERALLY SPONSORED RESEARCH AND DEVELOPMENT

This invention was made with government support under contract No. W911NF-17-3-003, subaward No. T0078, awarded by the U.S. Department of Defense through the Advanced Remanufacturing Institute (ARMI). The government has certain rights in the invention.

BACKGROUND

Tissue, such as skin tissue, vascular tissue, heart tissue, nerve tissue, umbilical cord tissue, and the like, are useful for various types of surgical procedures and wound treatments in humans and animals. The tissue used in surgical and/or graft procedures may be collected from humans or from animals. Some tissue, such as skin tissue, may also be artificially manufactured for testing and use. Examples of commercially available processed tissues include the Avance® Nerve Graft and Avive® Soft Tissue Membrane from Axogen, Inc. (Alachua, FL, US).

The processing, including but not limited to the decellularization or reduction of bioburden of, for example, non-autologous tissue for surgical implantation, can be time consuming and labor intensive, particularly in view of the many different solutions, enzymes, washes/rinses, or other liquid media to which the tissue may be exposed. Tissue processing can even result in unacceptable abrasion or other type of damage to the tissue, potentially compromising the surgical outcome with implantation, negatively impacting the tissue's integrity, and potentially prohibiting its ultimate surgical use.

Thus, there exists a need for more efficient and tissue-friendly tissue processing methods (e.g., methods that better preserve the integrity of the tissue and its structure).

SUMMARY

Herein described is a more automated approach, and components therefor, including tissue-processing containers useful for facilitating multistep processing of tissues. The tissue-processing containers may be stackable, including in a substantially air-tight and substantially liquid-tight manner, and each may allow for the processing of one or more tissue specimens per container. Also disclosed are systems incorporating the tissue-processing containers. Further disclosed is a transport housing for the tissue-processing containers. The tissue-processing containers, systems and general methods described herein may be used for the exposure of tissue to a variety of liquid media that may, for example, be useful for decellularization or reduction of bioburden, among other tissue processing efforts.

For example, provided are tissue-processing containers adapted for automation and multistep processing of tissues. The containers may possess an inner shape that is circular, but an outer shape that may be of any design or dimension adaptable for, for example, robotic manipulation and processing. The containers may have an overall cup appearance having a second inner diameter and a hole in the middle of the container that allows air and liquid to pass therethrough. The hole may be substantially circular, oval or elliptical in shape, or may be in the shape of a polygon. The outer wall, or first wall, of the tissue-processing container may be of any height and, in some embodiments, may be perpendicular and straight from the circular bottom, of the container, and, in other embodiments, may be slanted or flared outward from the center and/or not perpendicular from the circular bottom, of the container.

In some embodiments, a second wall may surround the hole in the circular bottom, of the container. The height of the second wall may be less than the height of the first wall. When placed on its circular bottom, the tissue-processing container may be open to the air on top, like a cup. The tissue-processing container may have one or more troughs fixedly attached to and/or integrally formed within the circular bottom of the tissue-processing container and surrounding the hole. The tissue-processing container may hold a first volume of liquid, and the one or more troughs may hold a second volume of liquid, wherein the first volume of liquid may be greater than the second volume of liquid.

In some embodiments, the tissue-processing container may further possess two mesh screens and two gaskets. A first mesh screen may be fixedly attached to the hole on an inner side surface of the tissue-processing container. The first gasket may surround the second wall surrounding the hole on the inner side surface of the tissue-processing container. A second gasket may be attachable to an outer side surface of the circular bottom, of the tissue-processing container and may have a diameter approximately equivalent to the second diameter. A second mesh screen may be attachable to an outer side surface of the circular bottom. The two mesh screens may be made of plastic polymer, pure or alloyed metal, resins, and/or an elastomeric polymer, such as rubber, or combinations thereof. In a particular embodiment, the first and/or second mesh screen may be comprised of polyamide, such as nylon. In a further embodiment, the first and/or second mesh screen may be comprised of nylon and polypropylene. The gauge or thread count of the mesh may be sufficient, such that any contact of it with the tissue does not result in unacceptable abrasion or damage to the tissue during the tissue processing. A sufficient gauge or thread count may be between about 300×300 threads per inch and about 500×500 threads per inch. For example, a suitable gauge or thread count of mesh may be about 325×325 threads per inch, or a suitable mesh may comprise openings of less than about 0.0017 inches.

In certain embodiments, the second mesh screen, when affixed or coupled to the outer side of the circular bottom, of the tissue-processing container, may not physically touch or associate with the outer side of the circular bottom of the tissue-processing container. That is, the second mesh screen may rest apart from the outer side of the circular bottom of the tissue-processing container.

In one embodiment, in order of height from top to bottom when the tissue-processing container rests with its circular bottom on a flat surface and its top open to the air above, the tallest feature may be the first wall, followed by the first mesh screen, the first gasket, the second wall, the one or more troughs, the circular bottom, the second mesh screen, and the second gasket, as depicted, for instance, in FIG. 1B.

In another embodiment contemplated herein, the tissue-processing container may be stackable with one or more additional tissue-processing containers, and when the tissue-processing containers are stacked, the middle holes of the containers in the stack may be in alignment. The middle holes of the tissue-processing containers in a stack may be of the same shape as one another, e.g., all circular in shape, all octagonal in shape, and so forth. In such an embodiment, the second gasket may form a substantially airtight and substantially watertight seal between two tissue-processing containers such that when full, substantially no air or liquid can escape from between two tissue-processing containers.

In some embodiments, the one or more troughs may be adjacent to and touching the first wall, in a particular embodiment. In another embodiment, the one or more troughs may be adjacent to and touching the second wall. In a further embodiment, the one or more troughs may not touch the first wall. In some embodiments, the one or more troughs may be semicircular in shape. In one embodiment, the one or more troughs may each be of sufficient size to accommodate at least one tissue specimen.

In one embodiment, the tissue-processing container may be made of a polymer or plastic polymer, such as, but not limited to, one or more of polycarbonate, polyetherimide, polyphenylsulfone, polystyrene, polysulfones, and polymethylpentene, and the like. In a particular embodiment, the tissue-processing container may be made of polymethylpentene (also known as NALGENE®, Thermo Fisher Scientific, Waltham, MA, US). The tissue-processing container may alternatively be comprised of glass or a silicate. In some embodiments, tissue specimens may not substantially adhere to the surfaces of the tissue-processing container.

In certain embodiments, the inner surface of the outer side of the circular bottom, of the tissue-processing container may be sloped from an outer diameter to an inner diameter, i.e., from the second diameter to the first diameter, toward the middle hole such that all liquid contacting the outer side drains through the middle hole when the tissue-processing container is oriented such the bottom is above the trough(s), i.e., the cup of the tissue-processing container is oriented upside down.

In a particular embodiment, the first volume may be between about 100 mL and 500 mL. In another such embodiment, the second volume may be between about 1 mL and 20 mL. In some embodiments, the first wall may comprise notches etched therein or affixed thereto to indicate fill level when liquid is added to the tissue-processing container.

As mentioned above, in certain embodiments, the first wall may have a thickness that is about 1 to 5 mm. In other embodiments, the tissue-processing container may comprise an outer, second container such that the outer dimensions of the tissue-processing container are different from the inner dimensions of the tissue-processing container. In such embodiments, the second container may be of a larger shape that can be, for example, a circle, oval, ellipse, or the like, or a polygon. The shape of the second container may facilitate handling or gripping of the tissue-processing container, including handling or gripping by robotic equipment and automated machinery. In one such embodiment, the second container may have a height that is approximately equal to the height of the first wall. The second container may be comprised of one or more of polycarbonate, polyetherimide, polyphenylsulfone, polystyrene, polysulfones, and polymethylpentene, and the like, or of glass or a silicate.

In certain embodiments, the height of the first wall may be from about 1 cm to about 10 cm. In an alternative embodiment, the tissue-processing container may further comprise a lid having a diameter approximately equal to the second diameter.

In further embodiments of the described tissue-processing container, two or more tissue-processing containers may be stacked on top of each other, wherein at least one tissue-processing container may be a bottom tissue-processing container and may be located below all the other tissue-processing containers in the stack, wherein at least one tissue-processing container may be a top tissue-processing container located above all the other tissue-processing containers in the stack. Optionally, the tissue-processing containers may each comprise a sloped outer face such that the outer edge of the bottom of a tissue-processing container extends further than the outer edge of the top of that same tissue-processing container, and when stacked, the outer edge of the bottom of a tissue-processing container extends beyond the outer edge of the top of the immediately adjacent tissue-processing container. In some embodiments, there may be additionally a base container located below the bottom tissue-processing container. The base container may possess substantially the same internal dimensions compared to the bottom tissue-processing container, such that the bottom tissue-processing container fits into the base container in a similar manner as one tissue-processing container fits into another tissue-processing container when stacked. The base container may further comprise a first nozzle attached to the first wall of the base container and extending into the inner side of the base container. Optionally, the first nozzle extending into the inner side of the base container may further connect to the middle hole of the adjacent tissue-processing container.

In such stacked tissue-processing container embodiments, there may also be in some embodiments a cap container that possesses substantially the same internal dimensions to the top tissue-processing container, such that the cap container fits with the top tissue-processing container in a similar manner as one tissue-processing container fits into another tissue-processing container when stacked. The cap container may further comprise a second nozzle attached to the first wall of the cap container and extending into the inner side of the cap container. Optionally, the second nozzle extending into the inner side of the cap container may further connect directly to the middle hole of the adjacent tissue-processing container. In the foregoing embodiments, each of the middle holes of all tissue-processing containers may be aligned, and further a substantially airtight and substantially watertight seal may be formed between each tissue-processing container. In some embodiments, substantially airtight and substantially watertight seals may be formed between the bottom tissue-processing container and the base container, as well as between the top tissue-processing container and the cap container, when a base container and a cap container are included in the stack.

In certain embodiments, the cap container and the base container may not, in and of themselves, be configured to or used to process tissue. For example, the cap container and/or the base container may be used for fluid management.

Some embodiments of the stacked tissue-processing containers may also comprise a cap container and a base container, the first and second nozzles may each be attached to a hose, and the hoses may conduct air and/or liquid therethrough.

In other embodiments, when in-use, each tissue-processing container of the stacked tissue-processing containers may contain one or more tissue specimens that may be in contact with the second circular mesh screen of the tissue-processing container in which the one or more tissue specimens in that container reside.

In some embodiments, the base container and the cap container may be identical and may each possess two nozzles. In an alternative embodiment, such cap and base containers may further possess a tilted disk bisecting a first wall of the cap and base containers such that the first nozzle may be positioned on or above the tilted disk, and the second nozzle may be positioned below the tilted disk in such a manner that, depending on how the cap and base containers are oriented, one may be placed on top of the stack of tissue-processing containers and the other may be placed below the stack of tissue-processing containers and liquid and/or gas, flows through the respective nozzles when desired. In such embodiments, the first and second nozzles may lie on opposite sides from each other in the first wall and may not come into contact with the middle hole of the bottom or top tissue-processing containers.

Also described herein are tissue-processing systems comprising one or more stacks of tissue-processing containers, each stack optionally including both a cap container and a base container, as described herein, and which further comprises a transport housing that encases one or more stacks of tissue-processing containers. Such transport housing may further be hermetically sealed and/or temperature-controlled to provide the desired conditions for the particular tissue processing step(s) (such as, but not limited to, incubation at precise temperatures without need for an incubator separate from the transport housing).

Tissue-processing systems may also include, in some embodiments, a programmable controller unit adapted to control various external inputs and hardware in a time-dependent manner, such as mechanical/electrical pumps that drive a flow rate of fluids and air into and out of the stacked tissue-processing containers, as well as temperature controllers, and other controls to adjust the speed of oscillation of the tissue-processing containers, via, for example, one or more shaker plates upon which the stacked tissue-processing containers may rest.

Tissue-processing systems may further include additional external hardware elements controlled by the controller, such as an incubator comprising a compartment sufficient in size to accommodate the transport housing, unless the housing itself is capable of controlling the temperature of the tissue-processing containers stacked within it. At least two hoses possessing a diameter approximately equal to a diameter of the first and the second nozzles are also contemplated as being part of such a system in order to transfer necessary fluids and gases into and out of the stack of tissue-processing containers.

As mentioned, in some embodiments, the system may comprise one or more electrical pumps attached to the hoses that are electronically controlled by the controller unit and that are adapted to be fixedly connected to at least one of the at least two hoses.

The hoses in such systems may be attached in turn to one or more media reservoirs comprising tissue-processing media and other liquid solutions useful in processing tissues. Also contemplated as part of such systems are one or more waste units adapted to be attached to one of the at least two hoses for the purpose of facilitating expulsion of liquid and gaseous waste from the tissue-processing containers.

Another contemplated external hardware element electrically controlled by the controller unit is a shaker comprising a surface adapted to accommodate the housing, or adapted to fit inside the housing such that the tissue-processing containers are oscillated at a desired frequency to maximize contact of the tissue specimen(s) with the surrounding media.

Also provided herein are methods of processing tissues. According to one tissue-processing method of the present disclosure, the tissue-processing container is oriented such that the inner side of the bottom is facing up. A tissue specimen may be placed in a trough of the tissue-processing container. A first tissue-processing media, which may comprise one or more enzymes, detergents, salt solutions, or other liquid media, may be added to the trough. The processing media may be added to the trough before, after, or at the same time as the tissue specimen is placed in that trough. These steps may be repeated with additional tissue-processing containers, and a stack of tissue-processing containers containing tissue specimens and the first processing media, may be formed. An individual tissue-processing container containing the tissue and first tissue-processing media, or the stack of such tissue-processing containers, may be incubated at a first temperature for a first period of time. The stack may or may not also comprise a cap container and a base container. The media of the tissue-processing container may thereafter be removed by tipping the stack of tissue-processing containers upside down, thereby draining the first tissue-processing media from the tissue-processing containers. The tissue specimens in the stack of tissue-processing containers may thereafter be rinsed/washed/soaked/or otherwise exposed to and potentially incubated with a second, third, fourth . . . or nth additional processing media, until the tissue-processing method is complete. In doing so, the stack of tissue-processing containers may be placed on a base container comprising a nozzle and a cap container comprising a nozzle may be placed on top of the stack of tissue-processing containers. A second tissue-processing media (which may comprise a fresh aliquot of the first tissue-processing media, or instead, a different tissue-processing media), may be filled through the bottommost container's nozzle. Optionally, the second tissue-processing media (or any additional tissue-processing media used in processing the tissue in further processing steps) may be added to the tissue-processing containers through the topmost container's nozzle. If filling, for example, through the nozzle of the bottommost container (which, when the stack is inverted to drain the first tissue-processing media, situates the cap container on the bottom of the stack) until the tissue-processing media fluid level reaches the second wall of the middle hole of a bottommost tissue-processing container in the stack, the second tissue-processing media may stop filling the bottommost tissue-processing container in the stack when its fluid level contacts the second wall of the middle hole of the bottommost tissue-processing container in the stack and any additional second tissue-processing media injected or otherwise filled into the bottommost tissue-processing container in the stack may exit through the middle hole and into a tissue-processing container stacked on top of the bottommost tissue-processing container in the stack, and so forth, thereby filling all tissue-processing containers in the stack with second tissue-processing media. In certain embodiments, the first tissue-processing media comprises at least one active enzyme, and in others the first tissue-processing media comprises more than one active enzyme.

In some embodiments, such methods may also comprise placing the tissue-processing containers comprising the second tissue-processing media in an incubator, and optionally incubating the tissue-processing containers at a second temperature (which may or may not be the same as the first temperature) for a second period of time (which may or may not be of the same duration of the first period of time). In certain embodiments, the first period of time and the second period of time may not be identical. In other embodiments, the tissue-processing containers (with or without incubator) may be located on a shaker. When used, the shaker may be operated at a sufficient periodicity to create a standing wave within the tissue-processing container. In additional embodiments, when the tissue-processing container stack is flipped upside down, the tissues may contact the second mesh screen.

The foregoing methods may, in additional embodiments, include additional steps, such as draining the second tissue-processing media from all of the tissue-processing containers, wherein the second tissue-processing media may exit through the middle holes and through the nozzle in the cap container (which is situated at the bottom of the stack of tissue-processing containers, if the cap container was included in the stack prior to its inversion). It should be appreciated that the terms "cap container" and "base container" may be used interchangeably and both refer to a single end container, depending on when that container was added to the stack of tissue-processing containers. That is, the container placed on top of the stack of tissue-processing containers prior to their inversion would be referred to as the cap container, and after inversion of the tissue-processing containers, would reside on the bottom of the stack. The container placed on top of the stack of tissue-processing containers after their inversion, would be referred to as the cap container, and would reside on the top of the inverted stack.

Aspects of the disclosure may be drawn to a container system. The container system may include a cup having an outer wall and an inner wall located radially inward of the outer wall, wherein a height of the inner wall may be less than a height of the outer wall. The system may also include a floor (also referred to in this disclosure as a "bottom") of the cup having a hole in substantially a middle of the floor, wherein the hole is located radially inward of the inner wall so that the inner wall surrounds the hole and the outer wall surrounds the inner wall. The system may further include at least two troughs located on an inner side of the floor of the cup, wherein the at least two troughs surround the hole, and wherein the at least two troughs are defined by two or more trough walls projecting from the inner side of the floor.

Various aspects may further include one or more of: a mesh screen covering the hole; a gasket configured to fixedly seal the mesh screen against the inner wall; a mesh screen located on an outer side of the floor, opposite the inner side; a gasket configured to seal the mesh screen against the outer side of the floor or an outer side of the outer wall; the outer wall may flare radially outward as it extends away from the floor of the cup; the floor may be sloped as it extends from the outer wall to the inner wall; an end of the cup opposite the floor may be uncovered; or substantially a middle of the floor may be the middle of the floor.

Other aspects of the disclosure may be drawn to a container system comprising a cup having a periphery defined by an outer wall, wherein the cup has a closed end and an open end, and an inner wall located radially inward of the outer wall, wherein a height of the inner wall is less than a height of the outer wall. The system may further include a floor defining the closed end of the cup, and a hole located in substantially a middle of the floor, wherein the hole is located radially inward of the inner wall so that the inner wall surrounds the hole and the outer wall surrounds the inner wall. The system may also include at least two troughs located on an inner surface of the floor of the cup, wherein the at least two troughs are defined by two or more trough walls projecting from the floor towards the open end of the cup, and wherein the two or more trough walls each have a height that is less than the height of the inner wall, as well as a first mesh screen extending across the hole, and a second mesh screen extending along an outer surface of the closed end of the cup.

Various aspects may further include one or more of: a first gasket configured to fixedly seal the first mesh screen across the hole, and a second gasket configured to seal the second mesh screen to the closed end of the cup; an end of the outer wall closest to the floor of the cup may define a first diameter, and an end of the inner wall closest to the floor of the cup may define a second diameter, smaller than the first diameter, and the hole may define a third diameter, smaller than the second diameter; the floor of the cup may be sloped radially outwards from the second diameter to the first diameter so that the floor adjacent the first diameter is located further from the open end of the cup than the floor adjacent the second diameter; a lid configured to removably cover the open end of the cup; or substantially the middle of the floor may be the middle of the floor.

Further aspects of the disclosure may be drawn to a container system comprising a first cup and a second cup, wherein each of the first cup and the second cup comprise an open end and a closed end, an outer wall extending from the open end to the closed end and defining a periphery, an inner wall located radially inward of the outer wall, wherein a height of the inner wall is less than a height of the outer wall, and a floor having a hole in substantially a middle of the floor, wherein the hole is located radially inward of the inner wall so that the inner wall surrounds the hole and the outer wall surrounds the inner wall, and at least two troughs located on an inner surface of the floor of the cup, wherein the at least two troughs are defined by two or more trough walls projecting from the inner surface of the floor. Further, the closed end of the first cup may be dimensioned to be received within the open end of the second cup such that the first cup is stackable with the second cup, and wherein the hole of the first cup is aligned with the hole of the second cup when the first cup is stacked with the second cup.

Various aspects may include one or more of: each of the first cup and the second cup may further comprise a mesh screen extending across the hole; each of the first cup and the second cup may further comprise a gasket fixedly securing the mesh screen across the hole; each of the first cup and the second cup may further comprise a second mesh screen extending along an outer surface of the closed end of the cup; each of the first cup and the second cup may further comprise a second gasket securing the second mesh screen along the outer surface of the closed end of the cup; the outer wall of the first cup and the outer wall of the second cup may each define a first diameter adjacent the closed end that is smaller than a second diameter adjacent the open end; the system may further comprise a base container having a first nozzle extending into an inner region of the base container, wherein the first nozzle is configured to fluidly connect to the hole of the first cup and a cap container having a second nozzle extending into an inner region of the cap container, wherein the second nozzle is configured to fluidly connect to the hole of the second cup; or substantially the middle of the floor may be the middle of the floor.

This Summary is provided to introduce a selection of concepts that are further described below in the Detailed Description. This Summary is not intended to identify critical or essential features of the claimed subject matter, nor is it intended to limit the scope of the claimed subject matter described more fully herein below.

BRIEF DESCRIPTION OF THE FIGURES

Reference is made herein to specific embodiments, as illustrated in the figures. The figures are not drawn to scale and any reference to dimensions in the figures or the following description are with reference to specific embodiments. It will be clear to one of skill in the art that variations of these dimensions are possible while still maintaining full functionality for the intended purpose. Such variations are specifically contemplated and incorporated into this disclosure notwithstanding the specific embodiments set forth in the following figures.

DETAILED DESCRIPTION

Definitions

Figure 1A:
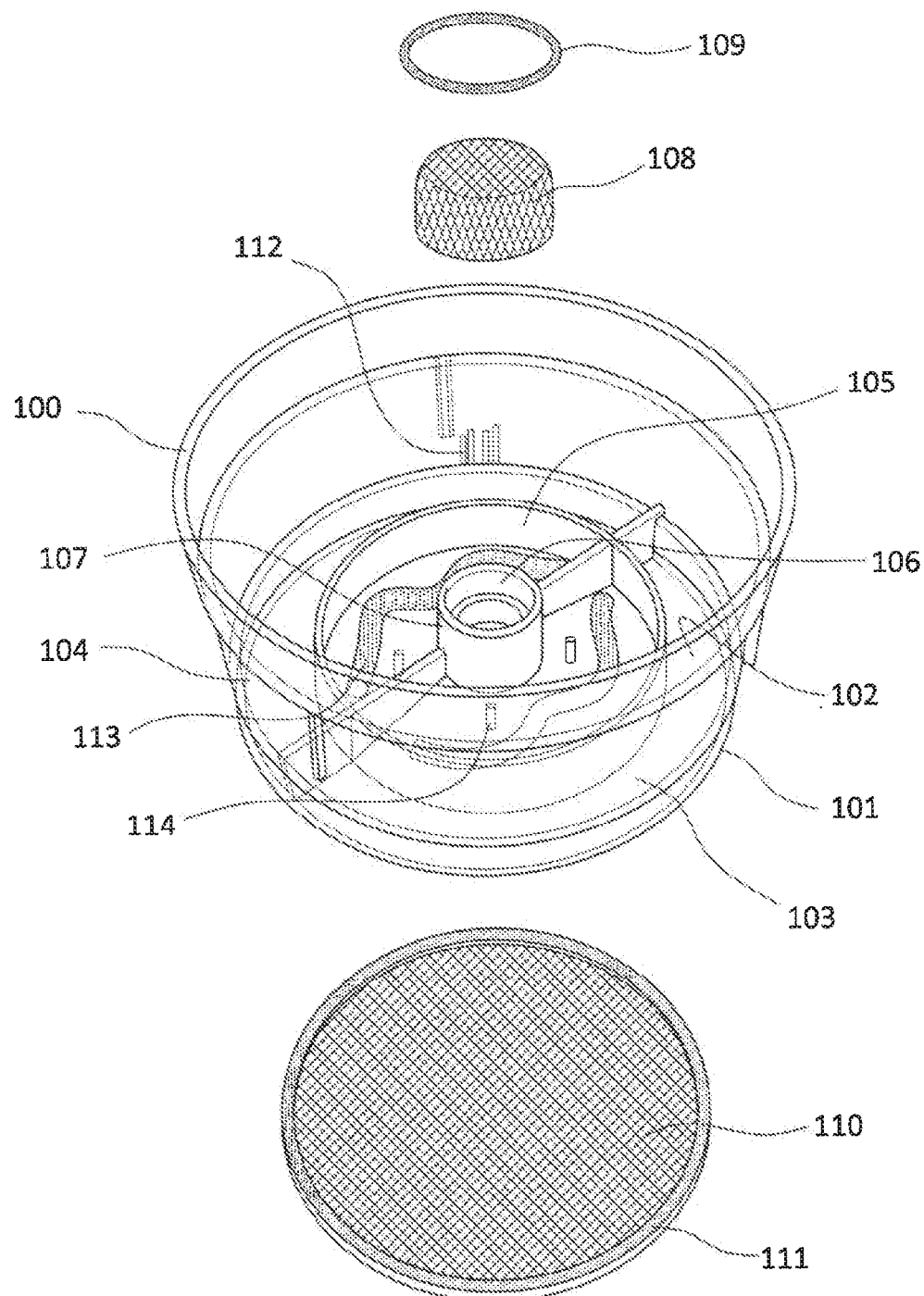
FIG. 1A is an exploded view of a tissue-processing container.

The term "gasket" means a ring-shaped object made of, e.g., a plastic polymer, rubber polymer, resin, or a mixture thereof, which acts to make a substantially airtight and/or substantially watertight seal between surfaces when fixedly engaged with both surfaces and pressure is applied thereon.

The term "trough," means an open container of any dimension or size that is fixedly attached, built into, integrally-formed, or otherwise formed as part of a surface of the tissue-processing container described herein and as shown, for instance, in FIGS. 1 and 2. The trough is open, allowing addition or subtraction of liquid and other materials into and out of the trough.

The term "tissue" means the nerve tissue or other type of tissue such as, but not limited to, cardiac, muscle, tendon, ligament, vascular, skin, SIS (small intestine submucosa), umbilical cord, dura, fascia, serosal, periostium, and other types of tissue. The tissue may be obtained from human or animal sources, and can be but is not limited to being of rodent, equine, canine, rabbit, porcine, primate, ovine or other ruminant, etc. derivation. The tissue may be naturally-procured from the human or animal sources, or it may be laboratory-grown.

The term "control unit" or "controller" indicates a powered hardware device including, for example, a controller or microcontroller, a processor or microprocessor with associated memory and peripherals, a field programmable gate array (FPGA), a programmable logic array (PLA) or a programmable logic controller (PLC), and/or a switching array. The control unit is configured to communicate with one or more external devices including, for instance, one or more mechanical pumps, incubators, and/or table shakers. The control unit serves to control, at least in part, operation of these external devices that are operationally connected to (e.g., plugged into and attached to or wirelessly connected to via Bluetooth, WiFi, or other suitable wireless connection) the control unit in such a manner that allows communication between the control unit and the external devices. Control units are generally programmable in a manner that allows an operator to input into the control unit one or more sets of instructions, e.g., for timing of power-on and power-off of external devices, setting of rates of external devices, such as flow rates, oscillation rates, temperatures, and/or other variables to operate the system including the tissue-processing container(s).

The term "adjacent," as used herein, may be used to refer to elements that are physically touching or are neighboring, e.g., separated by a small space or gap.

The term "middle" as used herein means center, and the term "substantially middle" means substantially center. Although embodiments described herein are described in terms of "middle," it is contemplated that each embodiment described may also be described in terms of "substantially middle."

In this disclosure, the singular forms "a," "an," and "the" include plural referents unless the context dictates otherwise. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. In this disclosure, unless stated otherwise, relative terms, such as, for example, "about," "substantially," and "approximately" are used to indicate a possible variation of +/−10% in the stated value. Moreover, in the claims, values, limits, and/or ranges of various claimed elements and/or features means the stated value, limit, and/or range +/−10%. In addition, the term "between" used in describing ranges of values is intended to include the minimum and maximum values described herein.

Tissue-Processing Containers

Provided are tissue-processing containers designed and adapted to promote efficient tissue processing and to minimize or reduce undesirable impact on the tissue itself during that processing (e.g., through too harsh agitation, abrasion resulting from contact with surrounding surfaces, damage due to too severe a flow of processing media, damage due to physical manipulation or over-manipulation of or pressure placed on the tissue, etc.). The tissue may be human or animal in origin, and may be naturally-procured therefrom or laboratory-grown.

The various processing steps accommodated by such tissue-processing containers may generally include, but are not limited to, washing, rinsing, soaking, or otherwise exposing the tissue to liquid tissue-processing media, for instance, one or more enzymes, detergents, salt solutions, and/or other desired liquid media and/or to one or more gases, appropriate for use in tissue processing. The tissue-processing containers and/or the tissue-processing media may be further incubated at or brought to a desired temperature. The tissue-processing containers may also be used to expose one or more tissue specimens to tissue-processing media and/or one or more gases, with agitation, for example, by use of a shaker. The tissue-processing containers described herein are multifunctional in that the containers accommodate different amounts of liquids in various orientations (bottom down, or bottom up, i.e., right-side-up, or upside-down, etc.). Further, because the tissue-processing containers are stackable, they accommodate parallel or simultaneous processing of one or more tissue specimens per container, and of multiple tissue specimens across a stack of containers, including as explained in further detail, below.

Referring now to the example of FIGS. 1A and 1n some embodiments, FIG. 1A shows an illustrative example of a tissue-processing container 100 that comprises several readily identifiable features and elements that distinguishes such containers from other state-of-the-art petri-dish type containers, vessels, flasks, or roller bottles, and the like. Namely, tissue-processing container 100, as shown in FIG. 1A, may be oriented in the right-side-up orientation and it is readily apparent that there may be a middle hole 106 transecting the circular bottom 101 of the tissue-processing container 100 and that the top of the tissue-processing container 100 may be open to the air. Circular bottom 101 possesses an inner side 102 and an outer side 103. Circular bottom 101, inner side 102, or outer side 103 may, in some aspects, be substantially circular. The middle hole 106 functions to allow air and liquid to pass therethrough during processing steps in methods using the tissue-processing container 100 for the processing of tissues, cells, and grafts. The middle hole 106 need not be of circular conformation as depicted in FIG. 1A, but may be of another configuration, such as an oval, ellipse or a polygon. Further, the circular bottom 101 and middle hole 106 may be the same shape or may be different shapes from one another.

Tissue-processing container 100 may be, in some embodiments, comprised of a polymer or plastic. In one embodiment, the tissue-processing container 100 is made of one or more of polycarbonate, polyetherimide, polyphenylsulfone, polystyrene, polysulfones, and polymethylpentene, and the like. In another embodiment, the tissue-processing container 100 is made of polymethylpentene. The tissue-processing container 100 may also be comprised of glass or a silicate. It will be appreciated that tissue-processing container 100 may be comprised of any material within the scope of the present disclosure.

Tissue-processing container 100 also possesses a first wall 104 possessing a first height that surrounds the container such that the container may hold a first volume of liquid. The first volume of liquid held by the container may be from about 100 mL and about 500 mL. In one embodiment, the first volume may be from about 150 mL to about 450 mL. In another embodiment, the first volume may be from about 200 mL to about 400 mL, or from about 250 mL to about 350 mL, or from about 275 mL to about 300 mL. In a particular embodiment, the first volume is about 275 mL. It will be appreciated that the size of the tissue-processing container and the features thereof may be increased or decreased so as to result in the accommodation of volumes of liquid greater than or less than those identified above.

The area above the tissue-processing container 100 as depicted in the orientation shown in FIG. 1A, may be open. On other words, there may not be a lid on top of the tissue-processing container 100 as depicted in FIG. 1A. In one embodiment, a lid may be provided sitting on top of the first wall 104 such that the inner side 102 is not open to air but instead is sealed by the lid. In one embodiment, the optional lid may possess substantially the same diameter as the tissue-processing container 100 such that when placed on top of the tissue-processing container 100 a seal may be formed that is substantially impermeable to air and/or liquid.

The first wall 104 of the tissue-processing container 100 is in some embodiments perpendicular or approximately perpendicular to the circular bottom 101. In other embodiments, the first wall 104 may be slanted, or flared outwards, from the bottom to the top of the tissue-processing container 100. That is, in some embodiments, the diameter defined by the top edge of the first wall 104 may be greater at the top than the diameter of the first wall 104 at the bottom of the tissue-processing container 100 where the first wall 104 is attached to circular bottom 101. In another embodiment, first wall 104 may extend in an upward and outward direction from where it is attached at circular bottom 101 to form a bowl shape as viewed from the side having rounded walls.

In one embodiment, since the tissue-processing container 100 may be intended to contain liquid media at certain times, the tissue-processing container 100 may also possess one or more fill level lines 112. The fill level lines may be horizontal and/or vertical. In one embodiment, there may be a single fill level line 112, but in other embodiments, there may be multiple fill level lines 112 indicating overfilling, underfilling, and exact target fill level. The one or more fill level lines 112 may be provided in or on the first wall 104 in any orientation, size, or shape, so long as when viewed by an operator or scanning instrument, it may be readily determined whether the tissue-processing container 100 is adequately filled with liquid media during processing, e.g., during a filling step, during exposure of the tissue to the tissue-processing media, and so forth. If the tissue-processing container does not contain the desired amount of tissue-processing media, it may indicate that the container is not being properly filled, that the stack has not been properly assembled, that there is a problem with the connection to the filling lines, that the substantially watertight seal has not been properly maintained within the stack of tissue-processing containers, that there is a broken seal or gasket, or other such problem, such that adjustments may be made to enable the desired processing of the tissue.

In some embodiments, middle hole 106, as depicted in FIG. 1A, may be defined by a second wall 107 having a second height that is less than the first height of the first wall 104. The relative heights of various features explained herein are depicted in side-view FIG. 1B.

Attached to the middle hole 106 on the side of the tissue-processing container 100 that is open to air is a first mesh screen 108 on the inner side 102 of the tissue-processing container, i.e., the side open to the air when the tissue-processing container 100 is placed in the orientation shown in FIG. 1A. The first mesh screen 108 may be made, e.g., of metal or a plastic polymer or resin or combination thereof and optionally extends over the top of the hole, i.e., extending along at least a portion of the second wall 107, so as to form a cap structure fully encompassing the opening of the middle hole 106. In one embodiment, the first mesh screen 108 may be comprised of metal. The metal may be, in one embodiment, a stainless steel or other alloy comprising one or more types of metal. In another embodiment, the first mesh screen 108 may be comprised of a pure metal, such as aluminum. The metal may be coated in some embodiments so as to reduce or minimize sticking of tissue specimens to the mesh screen. The gauge or thread count of the mesh may be sufficient, such that any contact of it with the tissue does not result in unacceptable abrasion or damage to the tissue during the tissue processing. In another embodiment, the first mesh screen 108 may be made of one or more plastic polymers. In a particular embodiment, the first mesh screen 108 is made of a polymer selected from one or more polyamides, or alternatively polybutylene terephthalate (PBT), polyethylene terephthalate (PET), polypropylene (PP), polycarbonate (PC), and the like, or a mixture thereof. In a particular embodiment, the first mesh screen 108 is made of polyamide. In a further embodiment, the first mesh screen is comprised of a nylon and/or polypropylene mesh.

In some embodiments, surrounding the first mesh screen 108 and fixedly attached thereto is a first gasket 109. First gasket 109 functions to fixedly seal the first mesh screen 108 against second wall 107. In some embodiments, first gasket 109 is comprised of an elastomer or other rubber polymer or mixture thereof.

Disposed on the inner side 102 of circular bottom 101 are one or more troughs 105. In one embodiment there are at least two troughs 105 disposed, fixedly attached to, built into, or otherwise formed as part of the inner side 102 of circular bottom 101. The one or more troughs 105 may be defined by one or more walls arising out of at an approximately perpendicular angle, but not necessarily perpendicular, to circular bottom 101. As depicted in FIG. 1A, the one or more troughs 105 are semi-circular in shape, but in other embodiments, the one or more troughs 105 are not semi-circular, and are instead rectangular, square, circular, triangular, or any other geometric shape. In one embodiment, the one or more troughs 105 may be located adjacent to middle hole 106, such that the one or more troughs 105 possess a common wall, i.e., the second wall 107, with the middle hole 106. In another embodiment, the one or more troughs 105 may be in direct contact with first wall 104 such that one or more of the walls defining the one or more troughs 105 is shared commonly with, or defined by, first wall 104. In another embodiment, the one or more troughs 105 may possess individual walls of their own that do not touch, extend to, or coincide with in any manner, either the second wall 107 or the first wall 104. In one embodiment, the tissue-processing container 100 possesses only a single trough affixed to the inner side 102 of the circular bottom 101. As used herein for discussion of the one or more troughs, affixed may include one or more separate features joined to one another, integrally formed with, built into, or the like, so that it is clear that affixed could include all such arrangements. In another embodiment, the tissue-processing container 100 may possess at least two troughs affixed to the inner side 102 of the circular bottom 101. In a further embodiment, the tissue-processing container 100 may possess at least three or four troughs affixed to, built into, or otherwise formed as part of the inner side 102 of the circular bottom 101.

The one or more troughs 105 may each accommodate one or more tissue specimens 113. In general, the one or more troughs 105 may also accommodate a liquid volume of between about 1 mL and 20 mL. For instance, in one embodiment, each trough 105 may accommodate a liquid volume of between about 2.5 mL and 17.5 mL, or between about 5 mL and 15 mL, or between about 7.5 mL and 12.5 mL, or between about 10 mL and 12.5 mL. It will again be appreciated that the volume of any one trough can be greater or less than the aforementioned volumes, depending on the size of the tissue-processing container and its features, and depending on the number of troughs present in the tissue-processing container. In some embodiments, each trough 105 included in a tissue-processing container 100 may be the same shape and size, while in other embodiments, one or more troughs 105 may have different shapes and/or sizes.

Attached to the outer side 103 of circular bottom 101 of the tissue-processing container 100 is optionally coupled a second mesh screen 110. In one embodiment, the second mesh screen 110 may be made of, e.g., metal or a plastic polymer or resin. In one embodiment, the second mesh screen 110 may be comprised of metal. In another embodiment, the metal may be a stainless steel or other alloy comprising one or more types of metal. In another embodiment, the second mesh screen 110 may be comprised of a pure metal, such as aluminum. The metal may be coated in some embodiments so as to reduce or minimize sticking of tissue specimens to the mesh screen. In another embodiment, the second mesh screen 110 may be made of one or more plastic polymers. In a particular embodiment, the second mesh screen 110 may be made of a polymer selected from one or more polyamides, or alternatively polybutylene terephthalate (PBT), polyethylene terephthalate (PET), polypropylene (PP), polycarbonate (PC), and the like, or a mixture thereof. In a particular embodiment, the second mesh screen 110 is made of polyamide. In a further embodiment, the first mesh screen is comprised of a nylon and polypropylene mesh. In any embodiment, the first and second mesh screens may be comprised of the same material, or of different materials. The gauge or thread count of the mesh should be sufficient, such that any contact of it with the tissue does not result in unacceptable abrasion or damage to the tissue during the tissue processing.

In some embodiments, a second gasket 111 may surround the second mesh screen 110. Second gasket 111 may function to seal the second mesh screen 110 against the outer side 103 of circular bottom 101. Second gasket 111 may be, in some embodiments, comprised of an elastomer or other rubber polymer or mixture thereof. In one embodiment, second gasket 111 may surround the outer side 103 of circular bottom 101 and may be fully in direct contact with first wall 104 along its entire inside circumference. In such an embodiment, second gasket 111 may be attached to the outside of first wall 104. In another embodiment, second mesh screen 110 may sit against outer side 103 of circular bottom 101. Thus, in some embodiments, second mesh screen 110 may possess an approximately identical diameter as circular bottom 101, and in other embodiment, second mesh screen 110 may possess a diameter that is larger than circular bottom 101. In another embodiment, second gasket 111 may fully surround and may be in contact with the entire outer circumference and edge of second mesh screen 110. In any embodiment, the first gasket and second gasket may be comprised of the same material, or of different materials.

In an alternative embodiment, the outer side 103 of circular bottom 101 may have affixed thereto one or more posts 114 extending downward toward the second mesh screen 110. The one or more posts 114 may be, in some embodiments, comprised of the same material as tissue-processing container 100. The one or more posts 114 may function to ensure that the second mesh screen 110 does not touch or come into contact with middle hole 106 on the outer side 103. In some embodiments, the one or more posts 114 may be circular in shape, having a diameter less than the diameter of middle hole 106. In one embodiment, tissue-processing container 100 may possess at least two posts 114. In another embodiment, tissue-processing container 100 may possess at least three posts 114. In a further embodiment, tissue-processing container 100 may possess at least four or more posts 114. The one or more posts 114 may not necessarily be perpendicular to circular bottom 101, but may be perpendicular in some embodiments. In other embodiments, the one or more posts 114 may be angled either towards first wall 104 or inward towards circular middle hole 106. The one or more posts 114 may be, in some embodiments, sufficiently long to extend just beyond the bottom of the tissue-processing container 100, and in other embodiments are only long enough to touch the surface upon which tissue-processing container 100 is resting in FIG. 1A.

In one embodiment, circular bottom 101 may not be flat or perfectly horizontal. That is, in some embodiments, circular bottom 101 may possess a pitch or an inverted funnel shape such that the circular bottom 101 height at the middle circular hole 106 may be higher than the circular bottom 101 height at the outside edge or circumference of circular bottom 101. (See, FIG. 1B). That is, in this embodiment, the outer side of the circular bottom 101 may be sloped from an outer diameter to an inner diameter towards the center middle hole 106 such that liquid contacting the outer side drains through the middle hole when the tissue-processing container 100 is oriented in an opposite orientation as depicted in FIG. 1A, i.e., in an upside-down-orientation, or flipped 180 degrees in the Y plane, such the circular bottom 101 is below the one or more troughs 105.

In a further embodiment of tissue-processing container 100, a third wall exists, which bisects circular bottom 101 on inner side 102 along the approximate diameter of circular bottom 101. In such an embodiment, the third wall may not extend through circular middle hole 106 but instead may only extend outward from middle hole 106 along the inner side 102 of circular bottom 101 to first wall 104. In such embodiments, the third wall may have a height that is less than or equal to the second height, i.e., the height of the second wall 107, and may form or function as one of the walls defining the one or more troughs 105.

In a further embodiment, tissue-processing container 100 may comprise an outer, second container. The purpose of the second container may be, for example, to provide a grippable shape and/or handhold grips or mounts for robotics used for automated processing, or other functionality, such as stacking stability, color-coding, labeling, or to otherwise aid in ready identification of particular tissue-processing containers. Thus, the second container may be of any shape, for example, a circle, oval, ellipse, or the like, or a polygon, and may be the same shape or a different shape compared to the inner container 100. The second container optionally has a height that is approximately equal to the height of the first wall. Optionally, the second container is made of the same material as the inner container 100. In another embodiment, the second container may be of a height greater than or less than the height of the first wall.

Such tissue-processing containers may be useful in that the one or more troughs 105 may be suitable for containing one or more tissue specimens 113.

Stacked Tissue-Processing Containers

Figure 2A:
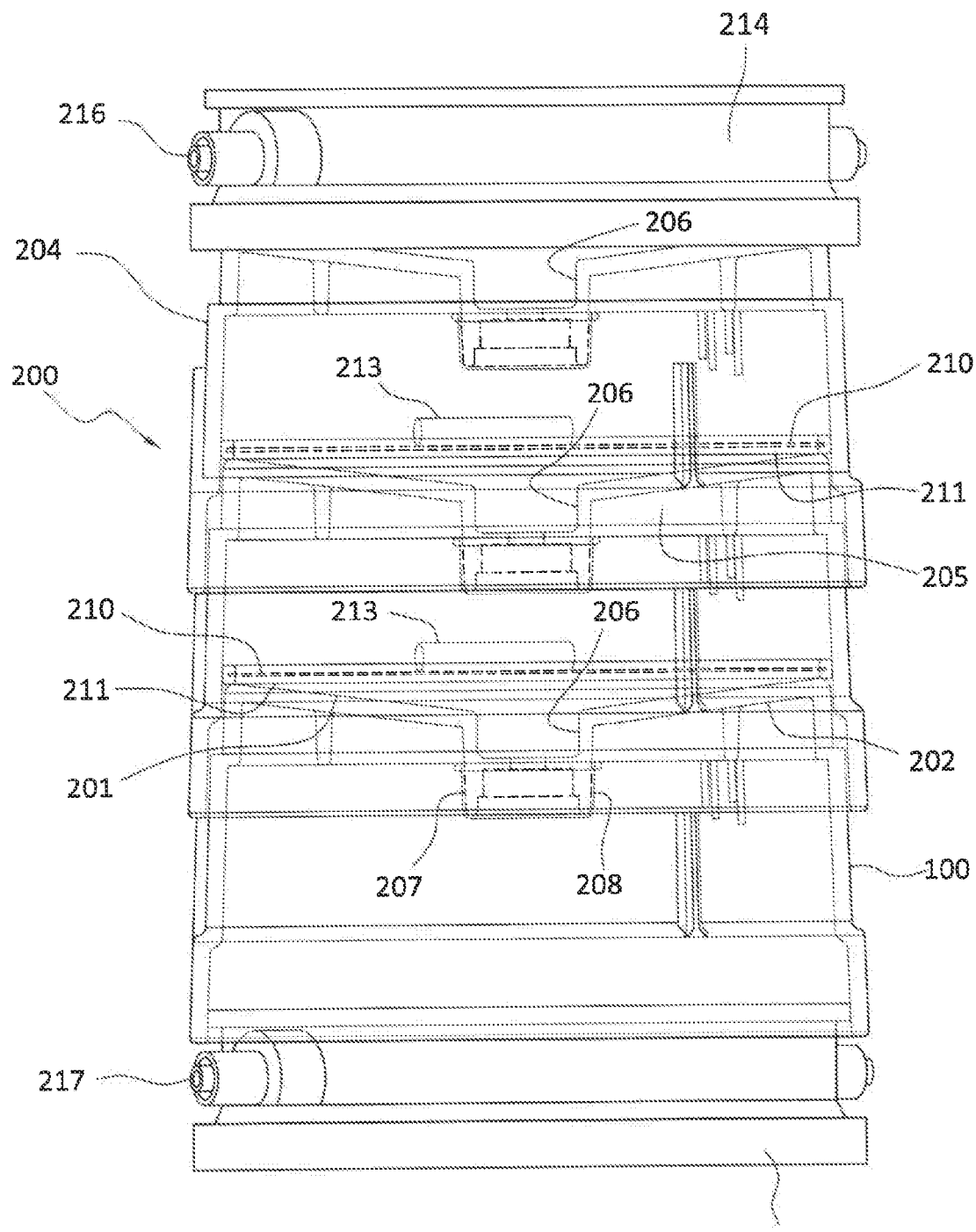
FIG. 2A is a side-view of a tissue-processing container stack including a base container and a cap container with nozzles.

Tissue-processing containers of the type described herein may be designed to be stacked one on top of the other to form a stack 200. (See, FIG. 2A, shown in inverted orientation). When stacking the tissue-processing containers, a second mesh screen 210 and/or a second gasket 211 may be placed on top of a tissue-processing container, and another tissue-processing container 100, which may be oriented in the position shown in FIG. 1A, may be placed on top of the second mesh screen 210 and/or second gasket 211. This process may be repeated until the desired-sized stack of tissue-processing containers is formed with second mesh screens 210, second gaskets 211, and tissue-processing containers 100. Upon completion of the stack of tissue-processing containers, the stack may be inverted as shown in FIG. 2A. In inverted stack 200, the middle holes 206 of each tissue-processing container 100 align with each other in a linear manner as depicted in FIG. 2A.

As previously mentioned, in one embodiment, the outer diameter of the first wall 204 of the tissue-processing container 100 is larger at the top than at the bottom, thereby creating an outward flare of the first wall 204 in an outward direction from the middle hole 206 from top to bottom. In this embodiment, flaring of the first wall 204 facilitates stacking such that the bottom of the container placed on top of the bottommost tissue-processing container 100 fits snugly into the top of the bottommost tissue-processing container, and so on throughout the stack 200.

In some embodiments, the second gasket 211 may enable the formation of a substantially airtight and substantially watertight seal between two adjacent tissue-processing containers 100 when the adjacent tissue-processing containers are stacked and compressed (e.g., pressure applied to compress the adjacent tissue-processing containers together). The second gasket 211, in some embodiments, may enable the substantially airtight and substantially watertight seal by pressure being applied between the circular bottom 201 of the tissue-processing container 100 and the top edge of the first wall 204 of the tissue-processing container 100 above, as oriented in FIG. 2A. In another embodiment, as described above, the second gasket 204 may fit snugly surrounding the circular bottom 201, and may touch only the inside surface of first wall 204 of the tissue-processing container 100 below it when the stack 200 is first being formed, thereby forming a the substantially watertight and/or airtight seal between the inner surface of first wall 204 of one tissue-processing container, and the outer edge of the circular bottom 201 of another tissue-processing container 100, with said second gasket 211 being sandwiched therebetween.

Referring also to the example of FIG. 2A and in some embodiments, the stack of tissue-processing containers may also comprise a cap container 215 and a base container 214 of substantially the same internal dimensions so as to facilitate stacking with the stack of tissue-processing containers. For example, each tissue-processing container of the stack of tissue-processing containers as shown in FIG. 2A is inverted (e.g., inverted relative to FIG. 1B). As depicted in FIG. 2A, the cap container 215 and base container 214 may each possess at least one nozzle 216, and 217, respectively, transecting through the outer wall of each of the cap container 215 and base container 214. The nozzles create a tubular channel from outside the cap container 215 and base container 214 into an interior space of the cap container 215 and base container 214, which may allow passage of liquid media or gas therethrough and into the adjacent tissue-processing container, through the middle hole of that tissue-processing container. In some embodiments, each of cap container 215 and base container 214 may include an open, interior space and through the open, interior space within each of cap container 215 and base container 214, liquid/and or gas may be transmitted through the hose connected to the nozzle and the external liquid/gas source, which is then transmitted into the open space of the bottom (originally the cap) container, and which then proceeds to each of the tissue-processing containers in the stack through their middle holes. In such an embodiment, a tube or hose connected directly or indirectly to a source of liquid (or gas, as the case may be, and including but not limited to a tissue-processing media) may be, in some instances, fixedly attached to the nozzles outside the stack 200 and when liquid, for example, flows therethrough, the liquid is conducted from outside the stack to inside the stack through the nozzles and, in the case of the base container 214, up through the middle hole 206 of the bottommost tissue-processing container 100 in the stack 200. Conversely, the cap container nozzle 216 likewise may transect the outer wall of the cap container 215 and proceed to a tube within the cap container 215 to a position just above the center middle hole 206 of the topmost tissue-processing container 100 in the stack 200. In this manner, liquid, for example, conducted into the topmost container 100 may proceed up through the topmost container center middle hole 206, then through the tube within the cap container 215, followed by an exit from the stack 200, via the nozzle 216. In some embodiments, the cap container 215 and base container 214 may be optionally added to the stacked tissue-processing containers 200 before tilting the stack 200 in the orientation shown in FIG. 2A. That is, the cap container 215 and base container 214 may be added to the stack either after or before inverting the stack of tissue-processing containers.

Figure 2B:
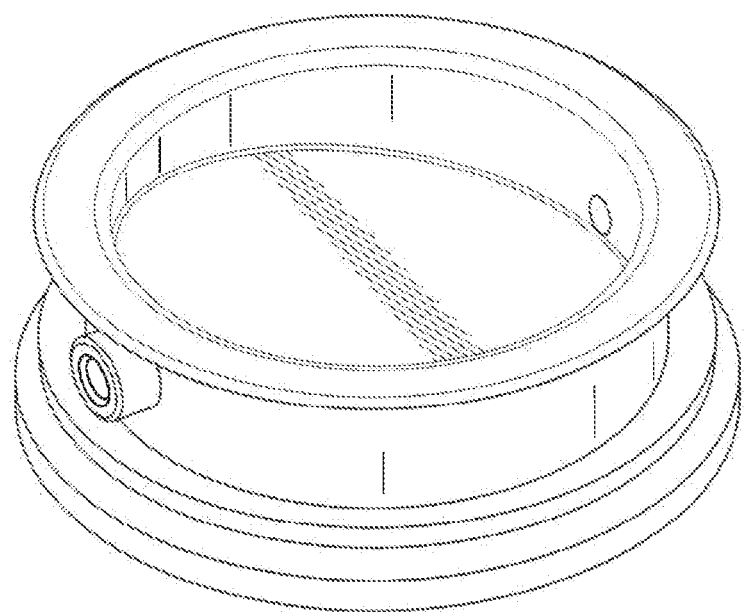
FIG. 2B is a perspective view of an alternative embodiment cap/base container.

An alternative embodiment of cap container 215 and base container 214 is provided in FIG. 2B. It can be readily deduced from the combined cap/base container depicted in FIG. 2B that the same cap/base element is used on both the top and the bottom of the stack.

Thus, when the tissue-processing containers 100 are stacked on top of each other to form a stack 200, and then inverted, and a cap container 215 and a base container 214 are added to the top and bottom of the stack 200, respectively, a substantially airtight and substantially watertight seal may be formed due to the pressure applied to the intervening second mesh screens 210 and second gaskets 211 between each tissue-processing container 100, and formed directly between the top-most and bottom-most tissue-processing containers and the cap/base container. Furthermore, in such an arrangement, liquid fed through nozzle 217 in the base container 214 will first fill the bottommost tissue-processing container 100 through the middle hole 206. The liquid level will gradually rise in the bottommost container and in one embodiment, will first contact the topmost edge of second wall 207 surrounding the middle hole 206.

As noted above, in one embodiment, the circular bottom 201 may not be flat. In this embodiment, the topmost edge of second wall 207, in the orientation depicted in FIG. 2A, would be the first inner side element contacted by the liquid as it rises inside the tissue-processing container 100. In doing so, an air pocket is formed above the final liquid level within the tissue-processing container 100, at the top of the tissue-processing container 100, such that the inner side 202 of the circular bottom 201 is not touching liquid fed through the circular middle hole 206. In this embodiment, the air pocket thus formed may serve the purpose of promoting or maximizing mixing of the liquid and exposure of the tissue to the liquid during various tissue processing steps (such as when the tissue-processing container stack 200 is being shaken by use of a shaker, as explained in more detail, below).

Further, if liquid and/or tissue 213 is present in the one or more troughs 205 when the two or more tissue-processing containers 100 are stacked on top of each other, when the stack 200 is inverted, the liquid and/or tissue 213 present in the one or more troughs 105 will come into contact with the second mesh screen 210. The liquid that was present in the one or more troughs 205 will subsequently pass through the second mesh screen 210 and through the circular middle hole 206 of the tissue-processing container 100 below. This flow of liquid that was previously contained by the one or more troughs 205 will continue through the stack until it reaches nozzle 217 and exits the stack 200. Meanwhile, the tissue specimen(s) 213 in each tissue-processing container 100 will rest on the mesh screen 210 below it.

Thus, in one embodiment, the tissue-processing container 100 may be comprised of a material that does not stick to or bind or adhere to the tissue 113 or 213. Furthermore, the first mesh screen 208 and second mesh screen 210 may be comprised of material that does not stick to or bind or adhere to the tissue 113 or 213. In certain embodiments, one or more components of the tissue-processing container 100 may be further coated with one or more additional chemicals, polymers, biological material, buffers, or other substances that reduce or minimize a negative impact on the tissue when in contact with such components of the tissue-processing container. In a particular embodiment, the tissue-processing container 100 is made of glass.

In another embodiment, each of the tissue-processing container 100 first walls 204 further possess a lip or skirt extension material that, when oriented as shown in FIG. 2A, overlaps with the outer circumference of circular bottom 201 of the tissue-processing container 100 underneath, such that a substantially airtight and substantially watertight seal is formed between each tissue-processing container 100 in the stack 200 by the second gasket 211 firmly or snugly fit between the outer surface of the first wall 204 of one tissue-processing container 100 on bottom, and the inner surface of the first wall 204 of another tissue-processing container 100 resting thereon in the stack 200. An additional function that may be served by said skirt or lip material of the first wall 204 is increased stability of the stack 200. The aforementioned first wall 204 extension material extending over the circular bottom 201 of each tissue-processing container 100 in the stack 200 may provide additional mechanical stability to the entire stack 200 that in some instances may be helpful to maintain substantially airtight and substantially watertight seals between each tissue-processing container 100 during processing steps, such as tilting or inverting the stack, moving the stack, and/or agitating the stack 200 by means of a shaker and the like.

Systems Comprising the Tissue-Processing Container

Figure 1B:
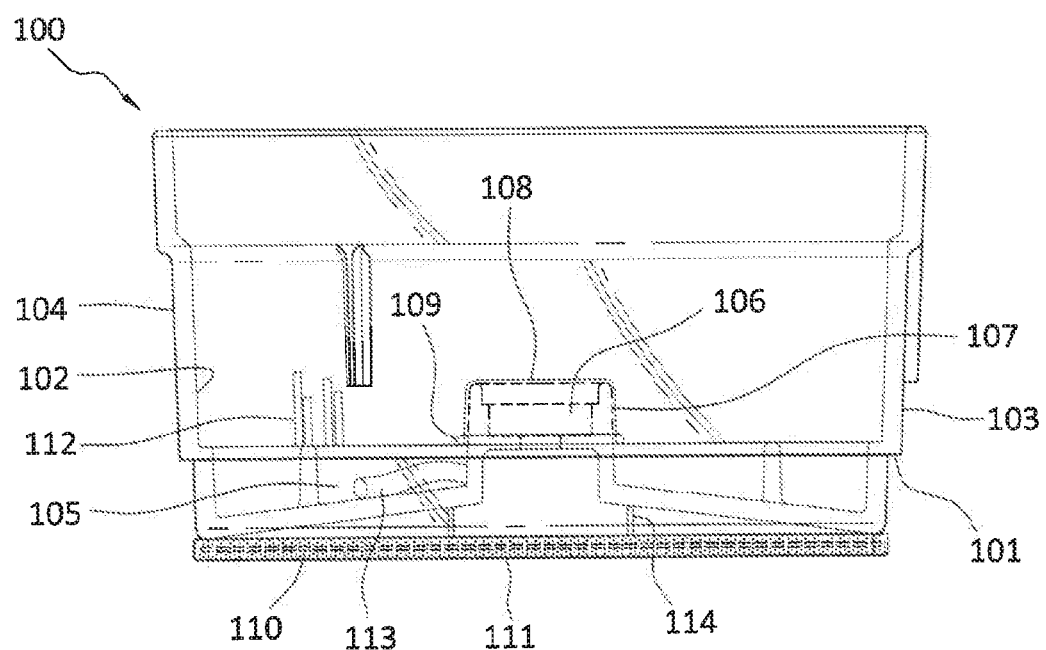
FIG. 1B is a side-view of a tissue-processing container.
Figure 3A:
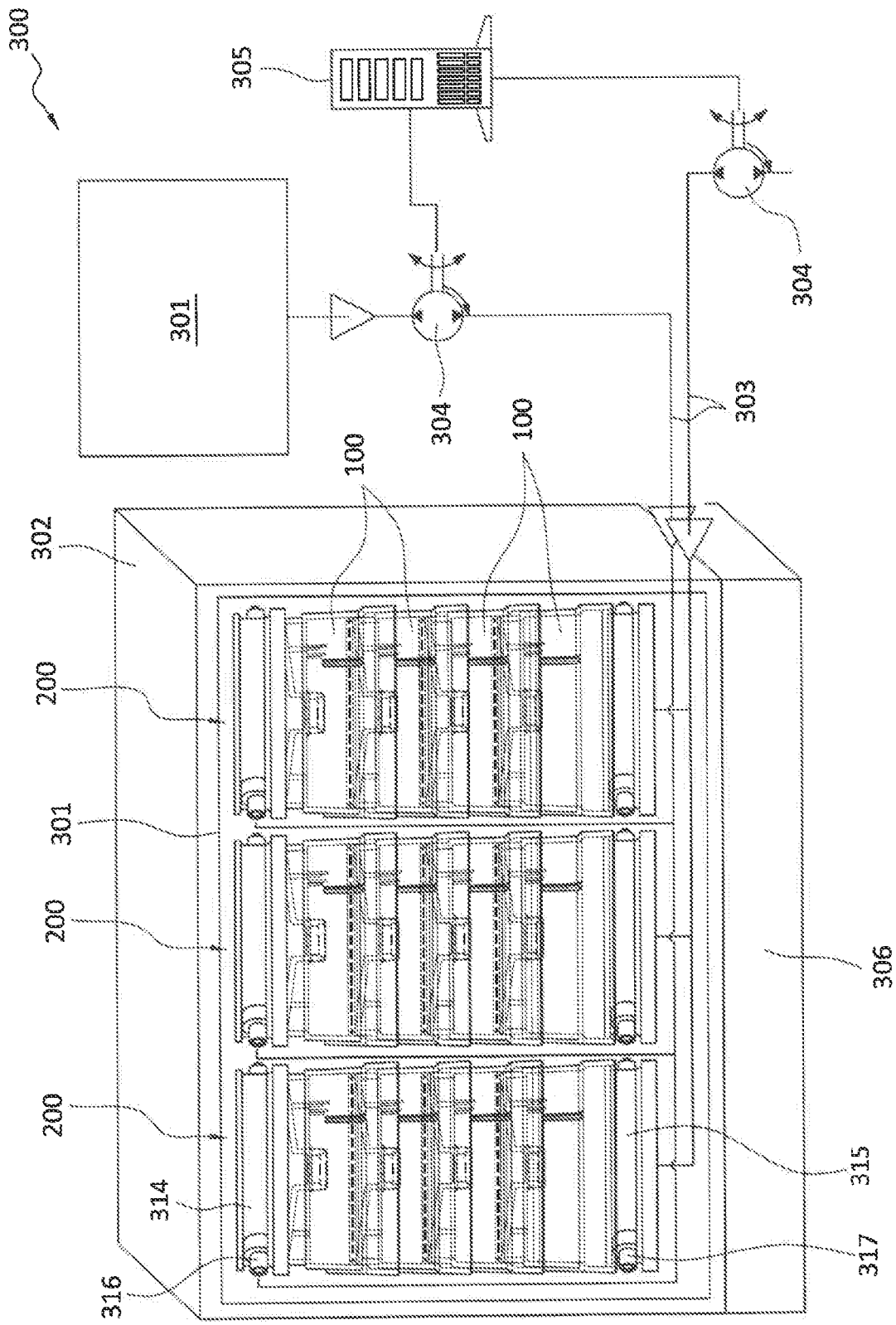
FIGS. 3A-3B depict systems comprising the tissue-processing container stack.
Figure 3B:
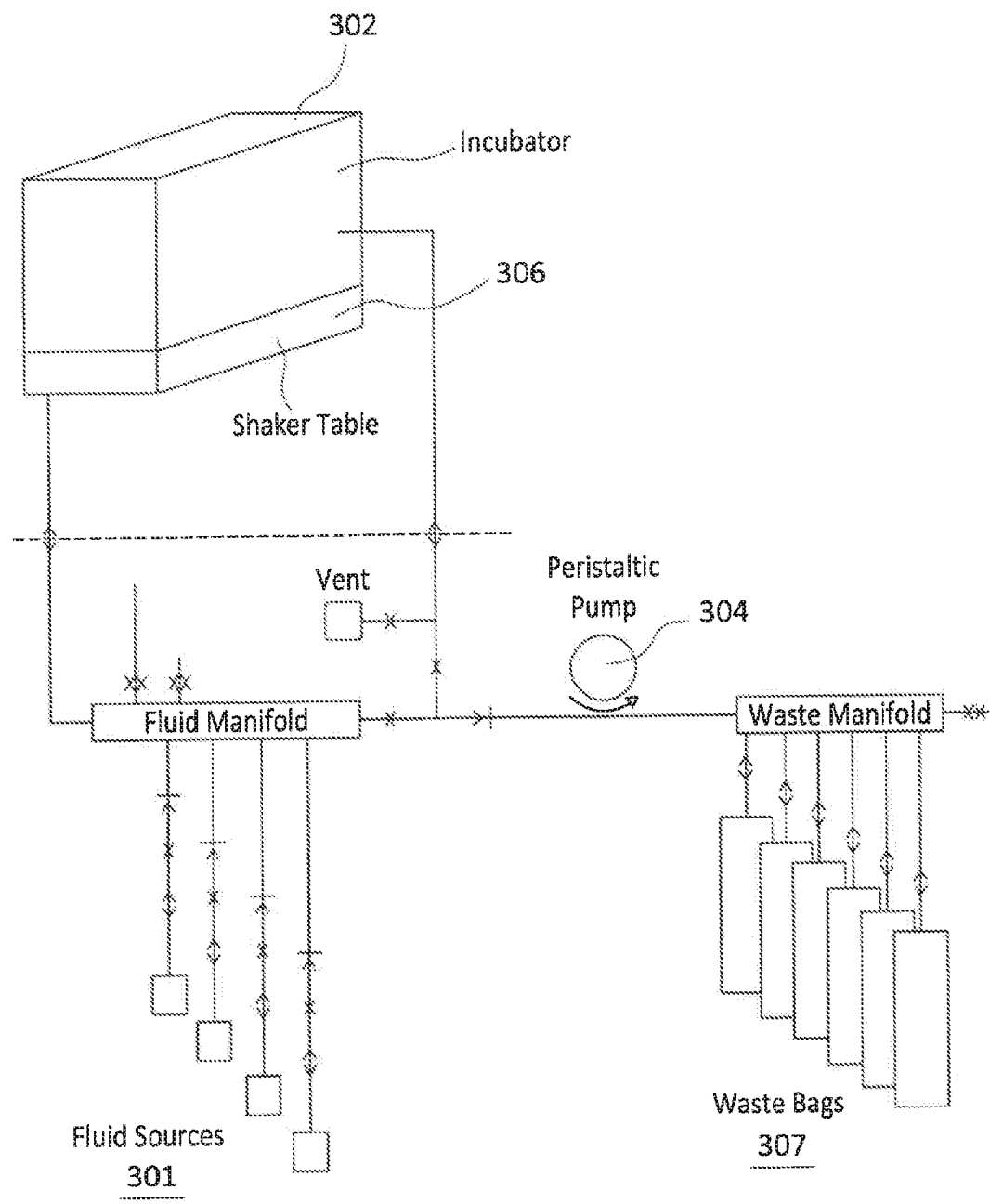

Further contemplated herein are systems 300 for processing tissue, comprising the tissue-processing containers 100 as shown, for instance, in FIGS. 3A and 3B, and as otherwise described herein. The contemplated systems comprise various components including, but not limited to, two or more tissue-processing containers 100 forming one or more stacks 200, optionally wherein each stack 200 further comprises a cap container 315 and a base container 314, as shown in FIG. 1B, as well as a transport housing 301 encasing the one or more stacks 200. The transport housing 301 is of sufficient dimension to encase one or more stacks 200. The transport housing 301 may serve a protective role to safely transport the one or more stacks 200 from a first location to a second location optionally desired during processing and therefore may act as a carrying case for the stacked tissue-processing containers. In some embodiments, the transport housing also comprises a stabilizer shroud for each stack of tissue-processing containers it will house. Such stabilizer shroud is used to maintain the stability of each stack of tissue-processing containers, and ensure each fits snugly into the transport housing so as to avoid accidental disassembly of the stacks, and to avoid breaking of the substantially airtight and substantially watertight seals between the tissue-processing containers, cap container and base container of each stack. The transport housing may further comprise a cover for the enclosing and/or sealing in of the one or more stacks of tissue-processing containers.

In some embodiments, transport housing 301 fits inside an incubator 302. In other embodiments, the one or more stacks 200 are placed directly into the incubator 302 and there is no need for transport housing 301 depending, e.g., on the processing steps and the tissue being processed. In another embodiment, transport housing 301 is optionally equipped with air regulators that serve to control and maintain proper gas requirements for any particular phase of the tissue processing. Such gas components include, but are not limited to, oxygen, nitrogen, carbon dioxide, and/or argon or other inert gases, as well as airborne moisture (water) to maintain appropriate humidity levels of the tissue during processing. In another embodiment, the incubator 302 is outfitted and equipped with such gas and humidity controls.

In one embodiment, the incubator 302 may rest on top of an oscillating shaker instrument 306. The oscillating shaker is not particularly limited and many are commercially available. However, in certain embodiments, the incubator 302, transport housing 301, and shaker 306 may all be controllable by a central processing unit or controller 305. In another embodiment, the one or more tissue-processing container stacks 200 may be placed directly onto a shaker 306 residing inside the incubator 302. Any number of such variations of system arrangements are possible so long as the tissue inside the tissue-processing containers 100 is exposed to appropriate atmospheric conditions, temperature, and mixing required for the particular processing of the tissue.

It should be noted that to achieve thorough exposure of the tissue to the tissue-processing media, the tissue-processing containers 100 may be oscillated, or shaken, at a rate that achieves this goal. It has been surprisingly discovered that by designing the tissue-processing containers 100 as described herein, which includes an air pocket above the liquid level line, and by oscillating or shaking the containers at a desired frequency, a standing wave of mixing may be established within the tissue-processing containers such that thorough and reproducible processing of the biological material is achieved. Optionally, the shaker 306 may comprise a tilting or tiltable function in addition to the shaking/oscillating function that is standard for commercially available laboratory shakers. Further, optionally, the tissue-processing stack 200 may also be tilted at a specific frequency to achieve thorough mixing and exposure of the tissue to the liquid media.

As shown in FIG. 3A, in some embodiments, the system may also comprise various tubes/hoses 303 providing ingress of fluids and egress of waste and air into a waste container 307. The hoses may attach to nozzles 317 and 316 for the purpose of providing channels to conduct liquid into and out of the tissue-processing containers 100. Also provided by the described systems herein are one or more electrical/mechanical solution pumps 304. The solution pumps may function to create pressure within hoses 303 thereby achieving ingress of fluid media solutions into and out of the tissue-processing stack 200 by way of the nozzles 317 and 316. Pumps 304 are optionally controllable and linkable to the controller unit 305 as with the other hardware elements described above.

Further provided in some embodiments of the described systems are one or more media reservoirs 301 comprising one or more tissue-processing media, for use in the processing (e.g., washing, rinsing, soaking, incubation, etc.) of the tissue specimens within the tissue-processing containers 100.

Additionally, provided are one or more programmable controller units 305 may be provided that may be linked electrically or by electrical signals, such as Wi-Fi, internet, etc., to the various hardware elements described above, i.e. the incubator 302, one or more pumps 304, shaker 306, housing 301, and the like. The linkage allows programmable controller unit 305 to automate the processing protocol for each biological tissue, cell, or graft within the tissue-processing containers. In some embodiments, the programmable controller unit may be provided with a user interface, programmable memory, computing chip, and other computer components necessary for running a software program that controls the start/stop function of each hardware component, as well as other variables specific for each hardware component, such as temperature, oscillation frequency, pitch or tilt, pump velocity, and the like. In such a manner, the described system may provide the operator with freedom to program one or more, e.g., all, variables into the programmable controller unit for processing of the tissue specimens within the tissue-processing containers. Such automation capability may provide various benefits, including efficiencies in saved time and materials, improved outcomes in processing of the tissues, uniformity and reproducibility in processing, etc.

Methods of Using the Tissue-Processing Container

The tissue-processing containers described herein may be useful in different tissue-processing protocols. The systems, e.g., automated systems, described above may be customizable to meet the needs of any desired tissue processing steps. To further describe such methods, a non-limiting, exemplary embodiment is provided below for illustrative purposes.

In one embodiment, the tissue-processing containers described herein may be employed in processing nerve tissue. In such methods, an empty tissue-processing container as described herein may be oriented such that the inner side of the bottom is facing upward. Optionally, the tissue-processing container may be placed on top of a base container. A debrided nerve tissue specimen may be placed into each trough of the tissue-processing container, and a first tissue-processing media may also be added to each trough containing a tissue specimen. Alternatively, the first tissue-processing media may be added to the trough prior to, or at the same time when the tissue specimen may be placed in the same trough. In one embodiment, the first tissue-processing media may comprise one or more active enzymes.

The first liquid media may be added manually using, for example, a calibrated pipette. Alternatively, the addition of one or more of the tissue specimens and the first tissue-processing media may be automated, for example, through a machine programed to deliver the tissue specimen and/or the tissue-processing media to the desired trough(s) in a reproducible manner.

Any portion of these steps may be repeated with additional tissue-processing containers, and tissue specimens, as desired to provide the desired number of tissue-processing containers containing tissue specimens and tissue-processing media. The additional tissue-processing containers may optionally be stacked. Stacking may occur such that the additional processing containers are stacked on top of each other after each has received the tissue specimen(s) and tissue-processing media, or tissue-processing container may be added to the stack before it has received one or more of the tissue specimen(s) and tissue-processing media, the tissue specimen and/or tissue-processing media may then be added thereto, and another tissue-processing container may be added atop thereof, and so forth, until the desired stack size is achieved.

In some embodiments, when proceeding to stack the tissue-processing containers, a cap container and a base container may be further added to the stack. A screen and a gasket may be included in the stack between each of the containers comprising the stack. The foregoing process may be repeated until the desired number of stacks are achieved, and then one or more stacks (e.g., three stacks) may be placed into the travel housing, and sealed therein. The travel housing containing the stacks of tissue-processing containers may be placed inside an incubator manually or via, for example, robotic arm, (or if the travel housing is so equipped, may itself be used to incubate the containers) at the desired first temperature for a first period of time. For example, if the first tissue-processing media is an enzyme, the travel housing containing the stacks of tissue-processing containers may be incubated at the optimal incubation temperature for that particular enzyme. Such temperatures, and the duration of incubation with each, are readily known or discernable by those of skill in the art for each enzyme that might be used. This same incubation process may be used for tissue-processing containers that have not been stacked and/or have been stacked but not placed inside a travel housing.

Upon completion of the first period of time, if the tissue-processing containers had not yet been stacked, each may be stacked one on top of the other as described above until a desired stack size is achieved. In some embodiments, added to the tissue-processing container stack are a base container and a cap container, though as pointed out above, the base container and the cap container may be added as part of and during the formation of the stack. In one embodiment, the tissue-processing containers may already comprise both the first mesh screen and second mesh screen, as well as the first gasket and second gasket prior to stacking. In other embodiments, the tissue-processing containers may comprise only the first mesh screen and first gasket, and the second mesh screens and second gaskets may be added only just prior to stacking the tissue-processing containers, adding in turn a tissue-processing container, a second gasket and then second mesh screen (this order can be reversed in some embodiments), following by a second tissue-processing container. This process of addition of these three components may then be repeated until the desired stack number is achieved.

After the stacked tissue-processing containers have completed the first incubation period, then the transport housing (or the individual stacks) may be inverted, to allow the first tissue-processing media to drain away from the tissue specimens and exit the tissue-processing containers. The first tissue-processing media then may exit through the nozzle in the cap container (which is now at the bottom of the stack) and out into one or more waste receptacles.

In some embodiments, the stacked tissue-processing containers and/or transport housing may then be returned to the incubator, or, depending on the tissue processing protocol, the next phase of the tissue process may be undertaken without use of the incubator. If the next step proceeds with use of the incubator, either prior to or after the return of the processing containers and/or transport housing containing the processing containers to the incubator, the incubator temperature may be adjusted to a second desired temperature for the next incubation period. In some embodiments, the cap container and base container may be attached to the appropriate tubing/hosing for automated or manual addition and potentially removal of the second tissue-processing media and/or liquid and/or gases. When the desired temperature is reached, a second liquid media may be added manually or automatically via a preprogrammed mechanism, into the stacked tissue-processing containers through the nozzle of each cap container (e.g., as shown in FIG. 3A where the stacked tissue-processing containers are inverted) and thus into each of the tissue-processing containers in the stack. As described above, the tissue-processing media travels through a hose and through the nozzle of the cap container, and into the hole of the bottommost tissue-processing container, filling up the bottommost tissue-processing container until the liquid level line reaches the tip or edge of the second wall of the middle hole. Thereafter, the liquid enters the middle hole of the tissue-processing container above the bottommost tissue-processing container and proceeds into the second tissue-processing container of the stack, and so forth, until the stack of tissue-processing containers each contains the appropriate amount of tissue-processing media. This process may result in an air pocket above the liquid level line in one or more or each of the tissue-processing containers, promoting optimal mixing and agitation of the liquid media.

At each stage, after all tissue-processing containers are filled, a shaker may optionally be used such that the tissue-processing containers are oscillated at a desired frequency. In one embodiment, to promote mixing or achieve maximal mixing, the revolutions per minute (rpm) of the shaker may be adjusted until a standing wave is achieved in the tissue-processing containers.

In one embodiment, before proceeding with processing, the fill level of each tissue-processing container is checked to confirm that an appropriate amount of the second tissue processing media is present in each of the tissue-processing containers. In one embodiment, the fill level is determined by visually inspecting each tissue-processing container. In another embodiment, the fill level is determined by visually inspecting the fill lines optionally placed on the first wall of each tissue-processing container. In a further embodiment, assessing the fill level of each tissue-processing container may be performed by a camera connected to the programmable controller unit, wherein optionally a software program is stored that distinguishes which tissue-processing containers are properly filled and which are not based on the data provided through the camera. Such inspection may be made to ensure there is no leakage between tissue-processing containers and to ensure that the set-up has been properly achieved.

The tissue-processing containers containing the second tissue-processing media may then be incubated at the desired second temperature for a second period of time. Afterward, the second liquid media may be evacuated from one or more, e.g., all, tissue-processing containers, by opening the nozzle in the cap container (e.g., as shown in FIG. 3A where the stacked tissue-processing containers are inverted) and allowing the second liquid media to drain out into one or more waste receptacles.

This process of filling and evacuating with liquid media may be repeatable for as many iterations as desired. The filling and draining steps may be controllable by the programmable controller unit described above. Likewise, the programmable controller unit in some embodiments is pre-programmed to control one or more external hardware devices in the system, such as, e.g., one or more of the shaker, incubator, one or more pumps, and etc. The above-described method therefore may be, in some embodiments, fully automated by the programmable controller unit in some embodiments or may be manual in other embodiments.

In one embodiment, the filling and draining of the stacked tissue-processing containers may include use of tissue-processing media for washing and/or rinsing the tissue specimens contained in the tissue-processing containers. In some embodiments, one or more of the steps may be repeated and/or one or more of the tissue processing media employed in each filling step may be the same or different in terms of components or composition. Thus, each step of filling and emptying the tissue-processing containers may be both automatable and customizable to the desired protocol for processing and for the particular type of tissue to be processed.

In one embodiment, the first period of time may be different from the second period of time. In another embodiment, the first and second period of time are the same. In one embodiment, the first temperature is the same as the second temperature. In a further embodiment, the first and second temperatures are different.

After processing the tissue, the stacked tissue-processing containers may be removed from the incubator and/or housing and detached from the base and cap containers. The stacks may then be disassembled to provide access to the processed tissue that rest on top of the second mesh screen at the bottom of each of the tissue-processing containers for further use.

Further modifications and alternative embodiments of various aspects of the methods and systems described herein will be apparent to those skilled in the art in view of this description. Accordingly, this description is to be construed as illustrative only and is for the purpose of teaching those skilled in the art the general manner of carrying out the disclosed methods and systems. It is to be understood that the forms of the disclosed methods and systems shown and described herein are to be taken as examples of embodiments. Elements and materials may be substituted for those illustrated and described herein, parts and processes may be reversed, and certain features of the disclosed methods and systems are capable of being utilized independently, all as would be apparent to one skilled in the art after having the benefit of this description of the disclosed methods and systems. Changes may be made in the elements described herein without departing from the spirit and scope of the disclosed methods and systems as described in the following claims.

The breadth and scope of the present disclosure should not be limited by any of the above-described exemplary embodiments, but should be defined only in accordance with the following claims and their equivalents. That is, the above examples are included to demonstrate various exemplary embodiments of the described methods and systems. It will be appreciated by those of skill in the art that the techniques disclosed in the examples represent techniques discovered by the inventor to function well in the practice of the described methods and systems, and thus can be considered to constitute optional or exemplary modes for its practice. However, those of skill in the art will, in light of the present disclosure, appreciate that many changes can be made in these specific embodiments that are disclosed and still obtain a like or similar result without departing from the spirit and scope of the described methods and systems.

What is claimed is:

1. A container system comprising:
   a cup having;
   an open end;
   a closed end;
   a periphery defined by an outer wall;
   an inner wall located radially inward of the outer wall, wherein a height of the inner wall is less than a height of the outer wall;
   a floor defining the closed end of the cup;
   a hole located in substantially a middle of the floor, wherein the hole is located radially inward of the inner wall so that the inner wall surrounds the hole and the outer wall surrounds the inner wall;
   at least two troughs located on an inner surface of the floor of the cup, wherein the at least two troughs are defined by two or more trough walls projecting from the floor towards the open end of the cup, and wherein the two or more trough walls each have a height that is less than the height of the inner wall;
   a first mesh screen extending across the hole; and
   a second mesh screen extending along an outer surface of the closed end of the cup.

2. The container system of claim 1, wherein the cup further has a first gasket configured to fixedly seal the first mesh screen across the hole, and a second gasket configured to seal the second mesh screen to the closed end of the cup.

3. The container system of claim 2, wherein an end of the outer wall closest to the floor of the cup defines a first diameter, and wherein an end of the inner wall of the cup, closest to the floor of the cup, defines a second diameter, smaller than the first diameter, and wherein the hole defines a third diameter, smaller than the second diameter.

4. The container system of claim 3, wherein the floor of the cup is sloped radially outwards from the second diameter to the first diameter so that the floor adjacent the first diameter is located further from the open end of the cup than the floor adjacent the second diameter.

5. The container system of claim 1, wherein the cup further has a lid configured to removably cover the open end of the cup.

6. The container system of claim 1, wherein substantially the middle of the floor of the cup is the middle of the floor of the cup.

7. The container system according to claim 1, wherein a gauge of the first mesh screen and/or the second mesh screen is about 300×300 threads per inch to about 500×500 threads per inch.

8. The container system according to claim 7, wherein the gauge of the first mesh screen and/or the second mesh screen is about 325×325 threads per inch.

9. The container system according to claim 1, wherein the first mesh screen and/or the second mesh screen comprises openings of less than about 0.0017 inches.

10. The container system according to claim 1, wherein the two or more trough walls are separate from one or both of the inner wall or the outer wall.

11. The container system according to acclaim 1, wherein the floor of the cup is sloped, so that the hole in the floor of the cup is higher than an outside edge of the floor of the cup when the inner side of the floor is facing upward.

12. The container system according to claim 1, comprising a plurality of cups.

13. The container system according to claim 12, wherein the plurality of cups are arranged in one or more stacks.

14. The container system according to claim 13, further comprising a housing, including a cover, configured to encase the one or more stacks of the plurality of cups.

15. The container system according to claim 13, further comprising a stabilizer shroud for each stack, of the one or more stacks.

16. The container system according to claim 13, further comprising an air regulator to control the flow of gas, and a humidity control to control one or more predetermined humidity levels of tissue during tissue processing in the plurality of cups.

17. The container system according to claim 13, further comprising one or more of:
- an incubator configured to control at least a temperature of tissue and tissue-processing media within the plurality of cups;
- a shaker configured to tilt and/or oscillate the plurality of cups;
- a camera configured to assess a fill level of the tissue-processing media within the plurality of cups; and
- one or more pumps connected to the container system via one or more hoses, and configured to supply the tissue-processing media to the plurality of cups, wherein the one or more pumps are configured to create pressure within the one or more hoses to achieve ingress of the tissue processing media into and egress of the tissue processing media out of the plurality of cups via a nozzle.

18. The container system according to claim 17, further comprising a controller, provided with a user interface, a programmable memory, and a computing chip, and being configured to execute a software program that controls one or more of the incubator, the shaker, the camera, and the one or more pumps.

* * * * *

UNITED STATES PATENT AND TRADEMARK OFFICE
CERTIFICATE OF CORRECTION

PATENT NO. : 12,215,305 B2
APPLICATION NO. : 18/441108
DATED : February 4, 2025
INVENTOR(S) : Daniel Barousse and Gerhard Andrew Foelsche Page 1 of 1

It is certified that error appears in the above-identified patent and that said Letters Patent is hereby corrected as shown below:

In the Claims

In Column 23, Line 66, in Claim 1, delete "having;" and insert --having:--; and
In Column 24, Line 54, in Claim 11, delete "acclaim" and insert --claim--.

Signed and Sealed this
Twenty-fifth Day of March, 2025

Coke Morgan Stewart
*Acting Director of the United States Patent and Trademark Office*